(12) United States Patent
Wensley

(10) Patent No.: US 12,290,105 B2
(45) Date of Patent: May 6, 2025

(54) ELECTRONIC SMOKING DEVICE WITH LIQUID PUMP

(71) Applicant: FONTEM VENTURES B.V., Amsterdam (NL)

(72) Inventor: Martin Wensley, Amsterdam (NL)

(73) Assignee: Fontem Ventures B.V., Amsterdam (NL)

( * ) Notice: Subject to any disclaimer, the term of this patent is extended or adjusted under 35 U.S.C. 154(b) by 997 days.

(21) Appl. No.: 16/978,159

(22) PCT Filed: Mar. 5, 2019

(86) PCT No.: PCT/EP2019/055390
§ 371 (c)(1),
(2) Date: Sep. 3, 2020

(87) PCT Pub. No.: WO2019/170638
PCT Pub. Date: Sep. 12, 2019

(65) Prior Publication Data
US 2021/0037883 A1 Feb. 11, 2021

(30) Foreign Application Priority Data
Mar. 7, 2018 (EP) .................................... 18160479

(51) Int. Cl.
*A24F 40/48* (2020.01)
*A24F 40/10* (2020.01)
*A24F 40/50* (2020.01)
*A24F 40/57* (2020.01)
*A61M 15/06* (2006.01)

(52) U.S. Cl.
CPC ............... *A24F 40/48* (2020.01); *A24F 40/50* (2020.01); *A24F 40/57* (2020.01); *A24F 40/10* (2020.01); *A61M 15/06* (2013.01); *A61M 2205/3368* (2013.01); *A61M 2205/8206* (2013.01)

(58) Field of Classification Search
CPC .......... A24F 40/48; A24F 40/50; A24F 40/57; A24F 40/10; A61M 2205/3368
See application file for complete search history.

(56) References Cited

U.S. PATENT DOCUMENTS

| 2003/0033055 | A1 | 2/2003 | McRae et al. |
| 2014/0069424 | A1 | 3/2014 | Poston et al. |
| 2020/0068949 | A1* | 3/2020 | Rasmussen ............. A24F 40/30 |

FOREIGN PATENT DOCUMENTS

| CN | 101116542 A | * | 2/2008 |
| WO | 2013060784 A2 | | 5/2013 |
| WO | 2016118645 A1 | | 7/2016 |
| WO | 2017108268 A1 | | 6/2017 |
| WO | 2017108429 A1 | | 6/2017 |

* cited by examiner

*Primary Examiner* — Jean F Duverne
(74) *Attorney, Agent, or Firm* — Dykema Gossett PLLC

(57) ABSTRACT

The invention relates to an electronic smoking device (10) with an atomizer/liquid reservoir portion (14) and to a method for generating vapor to be inhaled, by atomizing liquid, wherein the liquid is atomized by heating. In order to avoid that the liquid is overheated, the invention provides that the temperature applied for atomizing the liquid is controlled by controlling the pump rate of a liquid pump (35) of the electronic smoking device (10).

6 Claims, 3 Drawing Sheets

ELECTRONIC SMOKING DEVICE WITH LIQUID PUMP

FIELD OF INVENTION

The present invention relates generally to electronic smoking devices and in particular electronic cigarettes, and to methods for generating vapor to be inhaled, by atomizing liquid. The present invention in particular relates to electronic smoking devices having a refillable liquid reservoir.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapor.

An electronic smoking device can be adapted to allow refilling a liquid reservoir.

SUMMARY OF THE INVENTION

In accordance with one aspect of the present invention, there is provided an electronic smoking device, which comprises a power supply portion with a power supply. The electronic smoking device furthermore comprises an atomizer/liquid reservoir portion with a liquid reservoir adapted for storing liquid, and with an atomizer operable when connected to the power supply to atomize liquid stored in the liquid reservoir. The electronic smoking device comprises a liquid pump for pumping liquid from the liquid reservoir to the atomizer, and control electronics that are adapted to control the temperature of the powered atomizer by controlling the pump rate of the liquid pump.

In accordance with another aspect of the present invention, there is provided a method for generating vapor to be inhaled. The vapor is generated by atomizing liquid, in particular by heating the liquid. The temperature applied for atomizing the liquid is controlled by adjusting the supply rate of the liquid to be atomized.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
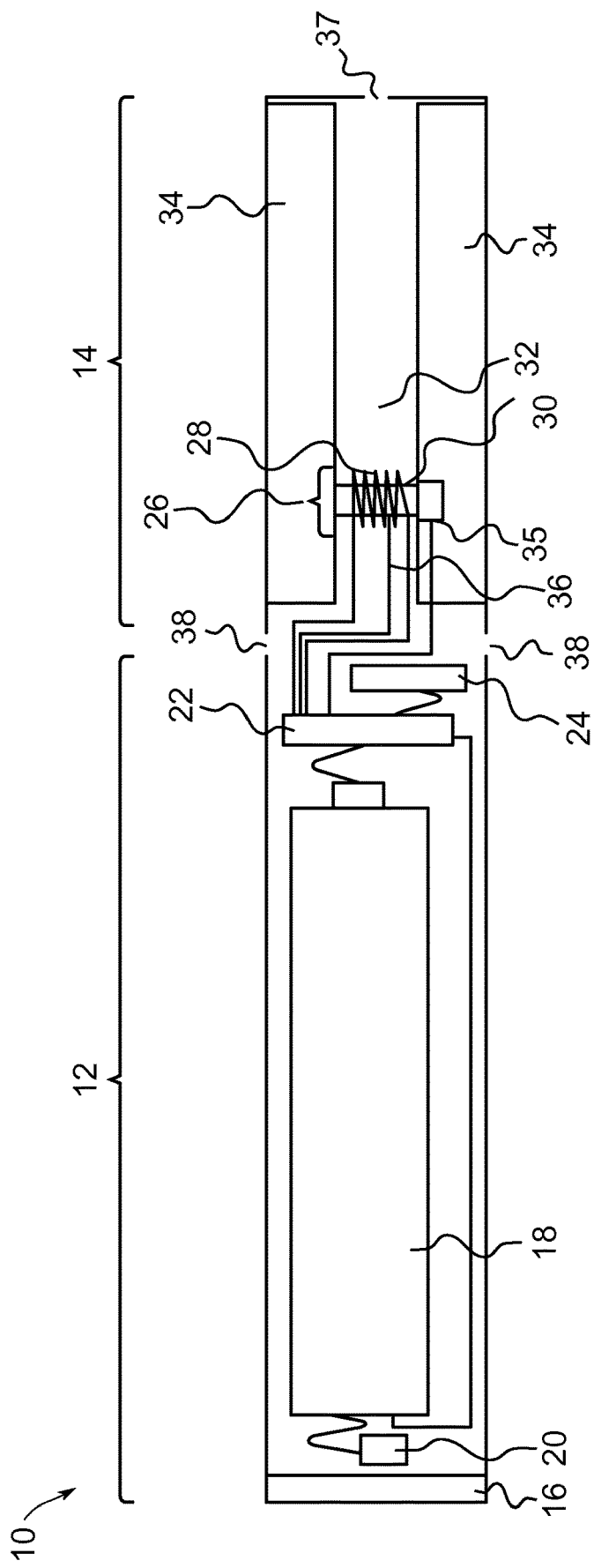
FIG. 1 shows an exemplary embodiment of an electronic smoking device in a schematic cross-sectional view.

Throughout the following, an electronic smoking device will be exemplarily described with reference to an e-cigarette. As is shown in FIG. 1, an e-cigarette 10 typically has a housing comprising a cylindrical hollow tube having an end cap 16. The cylindrical hollow tube may be a single-piece or a multiple-piece tube. In FIG. 1, the cylindrical hollow tube is shown as a two-piece structure having a power supply portion 12 and an atomizer/liquid reservoir portion 14. Together the power supply portion 12 and the atomizer/liquid reservoir portion 14 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 12 and atomizer/liquid reservoir portion 14 are typically made of metal, e.g. steel or aluminum, or of hardwearing plastic and act together with the end cap 16 to provide a housing to contain the components of the e-cigarette 10. The power supply portion 12 and an atomizer/liquid reservoir portion 14 may be configured to fit together by a friction push-fit, a snap-fit, or a bayonet attachment, magnetic-fit, or screw threads. The end cap 16 is provided at the front end of the power supply portion 12. The end cap 16 may be made from translucent plastic or other translucent material to allow a light-emitting diode (LED) 20 positioned near the end cap to emit light through the end cap. The end cap can be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 12 and the atomizer/liquid reservoir portion 14. FIG. 1 shows a pair of air inlets 38 provided at the intersection between the power supply portion 12 and the atomizer/liquid reservoir portion 14.

A power supply, preferably a battery 18, an LED 20, control electronics 22 and optionally an airflow sensor 24 are provided within the cylindrical hollow tube power supply portion 12. The battery 18 is electrically connected to the control electronics 22, which are electrically connected to the LED 20 and the airflow sensor 24. In this example, the LED 20 is at the front end of the power supply portion 12, adjacent to the end cap 16 and the control electronics 22 and airflow sensor 24 are provided in the central cavity at the other end of the battery 18 adjacent to the atomizer/liquid reservoir portion 14.

The airflow sensor 24 acts as a puff detector, detecting a user puffing or sucking on the atomizer/liquid reservoir portion 14 of the e-cigarette 10. The airflow sensor 24 can be any suitable sensor for detecting changes in airflow or air pressure, such as a microphone switch including a deformable membrane which is caused to move by variations in air pressure. Alternatively, the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The coil 28 may be positioned anywhere in the atomizer 26 and may be transverse or parallel to the liquid reservoir 34. The wick 30 and heating coil 28 do not completely block the central passage 32. Rather an air gap is provided on either side of the heating coil 28 enabling air to flow past the heating coil 28 and the wick 30. The atomizer may alternatively use other forms of heating elements, such as ceramic heaters, or fiber or mesh material heaters. Nonresistance heating elements such as sonic and piezo and jet spray may also be used in the atomizer in place of the heating coil.

The central passage 32 is surrounded by a cylindrical liquid reservoir 34 with at least one of the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include wadding soaked in liquid which encircles the central passage 32 with the ends of the wick 30 abutting the wadding. In other embodiments, the liquid reservoir 34 may comprise a toroidal cavity arranged to be filled with liquid and with at least one of the ends of the wick 30 extending into the toroidal cavity.

The electronic smoking device 10 comprises a liquid pump 35 for pumping liquid from the liquid reservoir 34 to the atomizer 26. In a flow path of the liquid from the liquid reservoir 34 to the atomizer 26, the liquid pump 35 is arranged, such that the liquid pump 35 can pump liquid stored in the liquid reservoir 34 to the atomizer 26. As exemplarily shown in FIG. 1, the liquid pump 35 is arranged inside of the liquid reservoir 34, such that the at least one end of the wick 30 is connected to the liquid pump 35 in a liquid receiving manner. The liquid pump 35 can be connected to an inner side wall of the liquid reservoir 34 in a sealing manner, such that liquid can reach the wick 30 exclusively via the liquid pump 35. Alternatively, the liquid pump 35 can be arranged outside of the liquid reservoir 34 in order to maximize storage capacity of the liquid reservoir. For example, the liquid pump 35 is arranged on the outer side of the liquid reservoir 34 that faces or borders on the central passage 32.

The liquid pump 35 is connected to the control electronics 22 in a control signal transmitting manner, such that the control electronics 22 can control the liquid pump 35, i.e. can control the pump rate of the liquid pump 35 and optionally can switch the liquid pump 35 on and off. By controlling the pump rate of the liquid pump 35, the control electronics 22 can change and, thus, control the temperature of the powered atomizer 26 via the liquid pump 35.

The electronic smoking device 10 optionally comprises a temperature sensor for measuring the temperatures of the atomizer 26, wherein the temperature sensor is not visible in FIG. 1, but is connected to the control electronics 22 by a signal line 36 in a measurement signal transmitting manner. The temperature sensor may contact the atomizer, for example the heating coil and/or the wick 30 and may for example be arranged at or inside of the heating coil. For example, the electric conductivity of the temperature sensor changes with the temperature. Alternatively, the temperature sensor is arranged at a distance to the atomizer. The temperature sensor may be an optical temperature sensor, for example a pyrometer.

Alternatively or additionally to the measurement of the temperature via the temperature sensor, the control electronics 22 are adapted to control the temperature of the powered atomizer 26 by controlling the pump rate based on the level of power supplied. The power supplied to the atomizer 26 is then used as a value that is representative for the temperature.

An air inhalation port 37 is provided at the back end of the atomizer/liquid reservoir portion 14 remote from the end cap 16. The air inhalation port 37 may be formed from the cylindrical hollow tube atomizer/liquid reservoir portion 14 or maybe formed in an end cap.

In use, a user sucks on the e-cigarette 10. This causes air to be drawn into the e-cigarette 10 via one or more air inlets, such as air inlets 38, and to be drawn through the central passage 32 towards the air inhalation port 37. The change in air pressure which arises is detected by the airflow sensor 24, which generates an electrical signal that is passed to the control electronics 22. In response to the signal, the control electronics 22 activate the heating coil 28, which causes liquid present in the wick 30 to be vaporized, creating an aerosol (which may comprise gaseous and liquid components) within the central passage 32. As the user continues to suck on the e-cigarette 10, this aerosol is drawn through the central passage 32 and inhaled by the user. At the same time, the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol, more liquid is drawn into the wick 30 from the liquid reservoir 34 by capillary action and thus is available to be converted into an aerosol through subsequent activation of the heating coil 28.

According to an exemplary embodiment, the control electronics 22 are adapted to control or predefine the level of power supplied from the power supply 18 based on a vapor requirement, e.g. the amount of vapor to be produced within a predefined time period or the vaporization rate, of a user of the electronic smoking device 10. For example, the vapor requirement can be determined based on the amount of air inhaled with a certain flow rate, e.g. the air mass flow, by the user. In order to determine the vapor requirement, the airflow sensor 24 or a mass air flow sensor may be used.

Some e-cigarettes are intended to be disposable and the electric power in the battery 18 is intended to be sufficient to vaporize the liquid contained within the liquid reservoir 34, after which the e-cigarette 10 is thrown away. In other embodiments the battery 18 is rechargeable and the liquid reservoir 34 is refillable. In the cases where the liquid reservoir 34 is a toroidal cavity, this may be achieved by refilling the liquid reservoir 34 via a refill port. In other embodiments the atomizer/liquid reservoir portion 14 of the e-cigarette 10 is detachable from the power supply portion 12 and a new atomizer/liquid reservoir portion 14 can be fitted with a new liquid reservoir 34 thereby replenishing the supply of liquid. In some cases, replacing the liquid reservoir 34 may involve replacement of the heating coil 28 and the wick 30 along with the replacement of the liquid reservoir 34. A replaceable unit comprising the atomizer 26 and the liquid reservoir 34 is called a cartomizer.

The new liquid reservoir 34 may be in the form of a cartridge having a central passage 32 through which a user inhales aerosol. In other embodiments, aerosol may flow around the exterior of the cartridge 32 to an air inhalation port 37.

Of course, in addition to the above description of the structure and function of a typical e-cigarette 10, variations also exist. For example, the LED 20 may be omitted. The airflow sensor 24 may be placed adjacent to the end cap 16 rather than in the middle of the e-cigarette. The airflow sensor 24 may be replaced with a switch which enables a user to activate the e-cigarette manually rather than in response to the detection of a change in air flow or air pressure.

Different types of atomizers may be used. Thus, for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively, the atomizer may use a piezoelectric atomizer to create an aerosol either in combination or in the absence of a heater.

Figure 2:
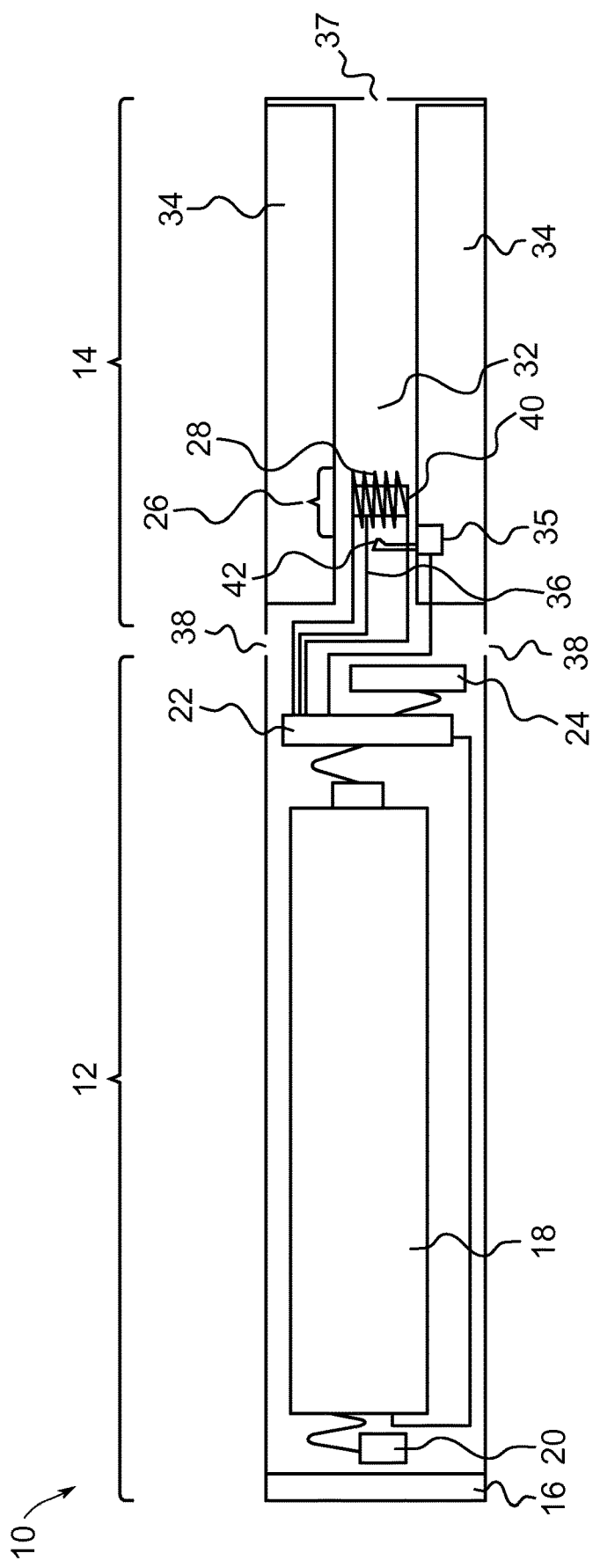
FIG. 2 shows another exemplary embodiment of an electronic smoking device in a schematic cross-sectional view.

FIG. 2 shows another exemplary embodiment of the electronic smoking device 10 in a schematic cross-sectional view. For elements, which correspond in form and/or function to elements of the previous exemplary embodiment, the same reference numerals are used. For the sake of brevity, only the differences with respect to the previous exemplary embodiment are discussed in the following.

In the exemplary embodiment of FIG. 2, the temperature sensor 40 is shown inside of the heating coil 28 and for exampled wrapped by the heating coil 28.

Independent of the embodiment and arrangement of the temperature sensor 40, FIG. 2 shows another exemplary embodiment of pumping liquid to the atomizer 26. The atomizer 26 is wickless, i.e. comprises no wick. In order to supply liquid from the liquid reservoir 34 to the atomizer 26 via the liquid pump 35, the electronic smoking device 10 comprises a nozzle 42, which is directed towards the atomizer 26 and in particular to the heating coil 28, and which is connected to the liquid pump 35 in a liquid receiving manner. Again, the liquid pump 35 can be arranged as explained above concerning the exemplary embodiment shown in FIG. 1.

Figure 3:
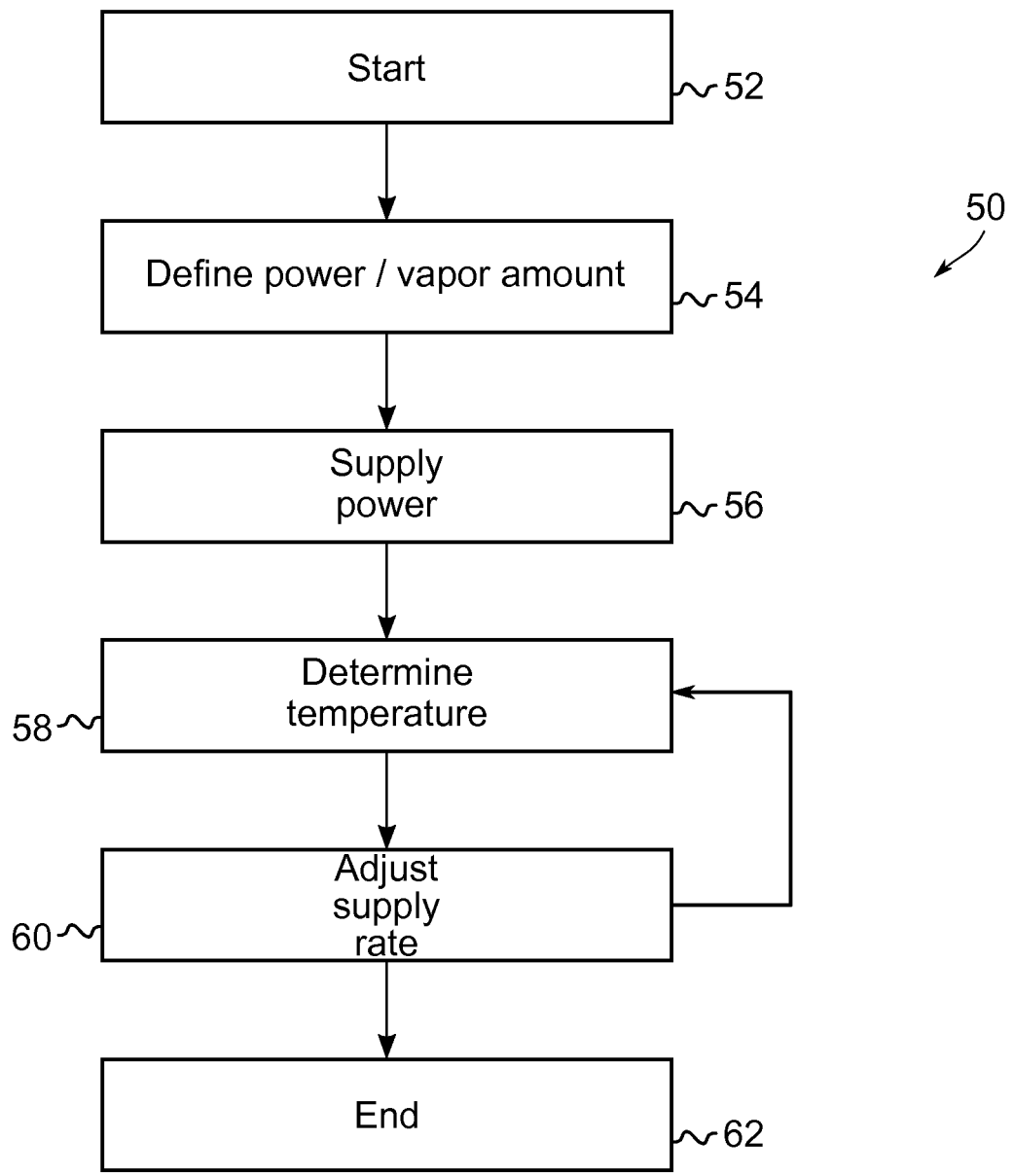
FIG. 3 shows an exemplary embodiment of a method for generating vapor to be inhaled, by atomizing liquid.

FIG. 3 shows an exemplary embodiment of a method for generating vapor to be inhaled, by atomizing liquid, wherein the liquid is atomized by heating the liquid, schematically as a flow-chart.

The method 50 starts with a first method step 52. For example, the begin of a puff is detected based on a signal generated with the airflow sensor 24.

After method step 52, method step 54 can optionally follow, in which the power and/or the amount of vapor to be produced during a predefined time period are determined. For example, the power and/or the amount of vapor to be produced are determined based on the flow rate of air along the airflow sensor 24 or a mass air flow sensor of the electronic smoking device 10.

As a next method step 56, the power defined in method step 52 or a predefined power is provided to the atomizer 26. Optionally, supply of liquid to the atomizer may be started simultaneously with the supply of power, or after a predefined time period after the start of the supply of power.

As a next method step 58, the temperature of the atomizer 26 is determined. The temperature of the atomizer depends from the power and the supply rate of liquid supplied to the atomizer 26. For example, the temperature is measured, e.g. with the temperature sensor 40. Alternatively or additionally, the power supplied to the atomizer 26, the amount of vapor to be produced during a predefined time period and/or the supply rate of liquid supplied to the atomizer 26 may be used to determine the temperature, e.g. via a mathematical calculation executed in the control electronics 22.

As a next method step 60, the supply rate with which the liquid pump 35 pumps the liquid to the atomizer 26 is adjusted in order to control the temperature. Hence, the supply rate can be determined based on the measured temperature or based on the power supplied to the atomizer 26 and/or the amount of vapor to be produced during a predefined time period.

During the puff, method steps 58 and 60 can be repeatedly executed in order to control the temperature at which the liquid is atomized.

The method 50 ends with a method step 62. For example, the end of the puff is detected based on a signal generated with the airflow sensor 24.

In summary, in one aspect, the electronic smoking device comprises a power supply portion with a power supply, and an atomizer/liquid reservoir portion comprising a liquid reservoir adapted for storing liquid, and an atomizer operable when connected to the power supply to atomize liquid stored in the liquid reservoir. The electronic smoking device further comprises a liquid pump for pumping liquid from the liquid reservoir to the atomizer, and control electronics that are adapted to control the temperature of the powered atomizer by controlling the pump rate of the liquid pump.

In another aspect, in summary, the method for generating vapor to be inhaled, by atomizing liquid, wherein the liquid is atomized by heating the liquid, comprising controlling the temperature applied for atomizing the liquid by adjusting the supply rate of the liquid to be atomized.

An advantage of the above aspects may be that overheating of the liquid, which may result in undesired taste of the vapor, is avoided without affecting the atomizing rate of the atomizer.

According to an embodiment of the electronic smoking device, the control electronics is adapted to control the temperature of the powered atomizer by controlling the pump rate based on the level of power supplied. An advantage of this embodiment may be that providing vapor at a stable atomizing rate is facilitated without the risk of overheating the liquid, wherein the temperature of the atomizer needs not to be measured directly, such that no separate temperature sensor is required.

According to an embodiment of the electronic smoking device, the control electronics are adapted to control the level of power supplied from the power supply based on a vapor requirement of a user of the electronic smoking device. According to an embodiment of the method, the level of power used for heating and vaporizing the liquid is determined based on an amount of vapor to be produced. An advantage of these embodiments may be that different amounts of vapor within a predetermined time period can be provided according to the users requirements, again without the risk of overheating the liquid.

For example, the vapor requirement can be determined based on vaping habit and/or vaping behavior, e.g. by determining and/or measuring the mass air flow along the air flow sensor and/or the atomizer.

According to an embodiment of the method, the supply rate is adjusted or controlled based on a level of power used for heating and vaporizing the liquid. According to an embodiment of the electronic smoking device, the control electronics are adapted to control the supply rate based on a level of power supplied to the atomizer. An advantage of these embodiments may be that the temperature of the atomizer needs not to be measure directly, such that no separate temperature sensor is required.

According to an embodiment of the electronic smoking device, the liquid pump is in a flow path of the liquid from the liquid reservoir to the atomizer, such that the liquid pump can pump liquid stored in the liquid reservoir to the atomizer, for example in order to supply the liquid directly onto the heating coil or to supply the liquid to the wick. For example, the liquid pump presses the liquid into the wick, such that the wick transports the liquid at a higher rate compared with the transportation rate of the wick without the pump. An advantage of this embodiment may be that liquid can be supplied at higher rates compared to an electronic smoking device without such a liquid pump.

According to an embodiment of the electronic smoking device, the liquid pump is arranged inside of the liquid reservoir. An advantage of this embodiment may be that flow of air through the electronic smoking device is not hindered by the liquid pump. For example, the liquid pump is connected to an inner side wall of the liquid reservoir in a sealing manner, such that liquid can reach the wick exclusively via the liquid pump.

According to an embodiment of the electronic smoking device, the liquid pump is arranged outside of the liquid reservoir. An advantage of this embodiment may be that storage capacity of the liquid reservoir is maximized. For example, the liquid pump is arranged on the outer side of the liquid reservoir that faces or borders on the central passage.

According to an embodiment of the electronic smoking device, the electronic smoking device comprises a temperature sensor for measuring the temperatures of the atomizer, wherein the temperature sensor is connected to the control electronics by a signal line in a measurement signal transmitting manner. According to an embodiment of the method, the temperature of the atomizer is determined and for example measured. An advantage of these embodiments may be that the temperature can be determined by measurement and, hence, directly and with high accuracy.

According to an embodiment of the electronic smoking device, the temperature sensor contacts the atomizer, for example the heating coil and/or the wick and may for example be arranged at or inside of the heating coil. An advantage of this embodiment may be that the temperature can be determined by measurement and, hence, directly and with high accuracy and, additionally, even fast temperature changes can be measured. For example, the electric conductivity of the temperature sensor changes with the temperature. Alternatively, the temperature sensor is an optical temperature sensor, for example a pyrometer, and/or the temperature sensor is arranged at a distance to the atomizer.

Independent of the embodiment and arrangement of the temperature sensor 40, FIG. 2 shows another exemplary embodiment of pumping liquid to the atomizer 26.

According to an embodiment of the electronic smoking device, the electronic smoking device comprises a nozzle, which is directed towards the atomizer and in particular to the heating coil, and which is connected to the liquid pump in a liquid receiving manner. An advantage of this embodiment may be that the supply or pump rate of the liquid can be changed swiftly. Another advantage of this embodiment may be that the temperature can be controlled by the supply or pump rate even if the atomizer is wickless, i.e. comprises no wick.

The temperature of the atomizer may depend from the power and the supply rate of liquid supplied to the atomizer. Hence, according to an embodiment of the method, the power supplied to the atomizer, the amount of vapor to be produced during a predefined time period and/or the supply rate of liquid supplied to the atomizer are used to determine the temperature, e.g. via a mathematical calculation executed in the control electronics.

LIST OF REFERENCE SIGNS 10 electronic smoking device
12 power supply portion
14 atomizer/liquid reservoir portion
16 end cap
18 battery
20 light-emitting diode (LED)
22 control electronics
24 airflow sensor
26 atomizer
28 heating coil
30 wick
32 central passage
34 liquid reservoir
35 pump
36 signal line
37 air inhalation port
38 air inlets
40 temperature sensor
42 nozzle
50 method
52 start
54 define power for atomizer
56 supply power to atomizer
58 determine temperature of atomizer
60 adjust supply rate to control temperature
62 End

The invention claimed is:

1. An electronic smoking device, comprising:
a power supply portion comprising a power supply; and
an atomizer/liquid reservoir portion comprising:
   a liquid reservoir adapted for storing liquid, and
   an atomizer operable when connected to the power supply to atomize liquid stored in the liquid reservoir,
wherein the electronic smoking device comprises:
   a liquid pump for pumping liquid from the liquid reservoir to the atomizer, and
   control electronics connected to the liquid pump in a control signal transmitting manner for controlling the temperature of the powered atomizer by controlling only the pump rate of the liquid pump.

2. The electronic smoking device according to claim 1, wherein the control electronics are adapted to control the temperature of the powered atomizer by controlling the pump rate based on the level of power supplied.

3. The electronic smoking device according to claim 1, wherein the control electronics are adapted to control the level of power supplied from the power supply based on a vapor requirement of a user of the electronic smoking device.

4. A method for generating vapor to be inhaled, by atomizing liquid, wherein the liquid is atomized by heating the liquid and the temperature applied for atomizing the liquid is controlled by adjusting only the supply rate of the liquid to be atomized.

5. The method according to claim 4, wherein the supply rate is adjusted based on a level of power used for heating and vaporizing the liquid.

6. The method according to claim 5, wherein the level of power used for heating and vaporizing the liquid is determined based on an amount of vapor to be produced.

* * * * *